(12) United States Patent
Casey et al.

(10) Patent No.: US 11,051,928 B2
(45) Date of Patent: Jul. 6, 2021

(54) FLOATING CAROTID FILTER

(71) Applicant: NEURAVI LIMITED, Galway (IE)

(72) Inventors: Brendan Casey, Galway (IE); David Vale, Galway (IE)

(73) Assignee: NEURAVI LIMITED, Galway (IE)

(*) Notice: Subject to any disclaimer, the term of this patent is extended or adjusted under 35 U.S.C. 154(b) by 116 days.

(21) Appl. No.: 16/381,449

(22) Filed: Apr. 11, 2019

(65) Prior Publication Data
US 2020/0323615 A1 Oct. 15, 2020

(51) Int. Cl.
*A61F 2/01* (2006.01)
*A61F 2/95* (2013.01)
*A61B 17/3207* (2006.01)

(52) U.S. Cl.
CPC ............... *A61F 2/013* (2013.01); *A61F 2/95* (2013.01); *A61B 17/3207* (2013.01); *A61F 2/011* (2020.05)

(58) Field of Classification Search
CPC .. A61F 2/013; A61F 2/011; A61F 2/01; A61F 2/0103; A61F 2/0105; A61F 2/0108; A61F 2/012; A61F 2/014; A61F 2/90; A61F 2/95; A61F 2/82; A61F 2/07; A61F 2/954; A61F 2/2436; A61F 2/844; A61F 2002/9528; A61F 2250/0023; A61B 17/12109; A61B 17/221; A61B 17/120222; A61B 17/12168; A61B 17/12027; A61B 17/12118; A61B 17/135; A61B 2017/2215; A61B 2017/2206; A61B 2017/22069; A61B 2017/22038; A61B 2018/00267; A61B 2018/0041; A61B 2018/0212; A61M 2025/0042; A61M 2025/0681; A61M 2210/12
See application file for complete search history.

(56) References Cited

U.S. PATENT DOCUMENTS

| | | | |
|---|---|---|---|
| 7,229,462 B2 | 6/2007 | Sutton et al. |
| 7,316,702 B2 | 1/2008 | Joergensen et al. |
| 8,267,956 B2 | 9/2012 | Salahieh et al. |
| 8,372,108 B2 | 2/2013 | Lashinski |

(Continued)

OTHER PUBLICATIONS

"Jadhav, "Emergent Management of Tandem Lesions in Acute Ischemic Stroke", Dec. 11, 2018, Stroke, 50, 428-433" DOI: 10.1161/STROKEAHA.118.021893.) The online-only Data Supplement is available with this article at https://www.ahajournals.org/doi/suppl/10.1161/STROKEAHA.118.021893 (Year: 2018).*

(Continued)

*Primary Examiner* — Elizabeth Houston
*Assistant Examiner* — Lauren Dubose
(74) *Attorney, Agent, or Firm* — Troutman Pepper Hamilton Sanders LLP

(57) ABSTRACT

Shortly after completing a thrombectomy procedure, a temporary carotid filter can be deployed downstream of an occlusion not treated by the thrombectomy (e.g. a carotid lesion having plaque buildup), and the temporary carotid filter can remain in place during the patient's recovery period following the ischemic stroke until a procedure to treat the remaining occlusion is completed and antiplatelet therapy is administered. The temporary carotid filter can anchor in place while deployed with or without being tethered to a wire extending through the patient's Femoral Artery.

18 Claims, 10 Drawing Sheets

(56) References Cited

U.S. PATENT DOCUMENTS

| | | |
|---|---|---|
| 8,795,322 B2 | 8/2014 | Cully et al. |
| 8,801,750 B2 | 8/2014 | Cully et al. |
| 9,198,690 B2 | 12/2015 | Steinmetz |
| 9,220,522 B2 | 12/2015 | Fulkerson et al. |
| 9,283,066 B2 | 3/2016 | Hopkins et al. |
| 9,345,565 B2 | 5/2016 | Fifer et al. |
| 9,492,264 B2 | 11/2016 | Fifer et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,943,395 B2 | 4/2018 | Fifer et al. |
| 9,943,396 B2 | 4/2018 | Galdonik et al. |
| 9,980,805 B2 | 5/2018 | Fifer et al. |
| 10,058,411 B2 | 8/2018 | Fifer et al. |
| 2003/0130680 A1 | 7/2003 | Russell |
| 2005/0267512 A1* | 12/2005 | Osborne ............. A61F 2/01 606/200 |
| 2007/0244504 A1 | 10/2007 | Keegan et al. |
| 2009/0182268 A1* | 7/2009 | Thielen ............. A61M 25/0138 604/95.04 |
| 2010/0204772 A1* | 8/2010 | Holzer ............. A61F 2/013 623/1.11 |
| 2011/0046655 A1 | 2/2011 | Arnott et al. |
| 2012/0035650 A1* | 2/2012 | Linder ............. A61F 2/013 606/200 |
| 2013/0035628 A1* | 2/2013 | Garrison ............. A61M 25/0662 604/8 |
| 2013/0172977 A1 | 7/2013 | Forde et al. |
| 2014/0163603 A1 | 6/2014 | Zajarias |
| 2016/0158038 A1* | 6/2016 | Teitelbaum ............. A61F 2/07 623/1.11 |
| 2016/0220265 A1 | 8/2016 | Pokorney et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |

(56) References Cited

U.S. PATENT DOCUMENTS

2017/0340383 A1  11/2017  Bloom et al.
2017/0348014 A1  12/2017  Wallace
2017/0348514 A1  12/2017  Guyon et al.

OTHER PUBLICATIONS

Extended European Search Report issued in corresponding European Patent Application No. 20 16 9419 dated Aug. 4, 2020.

* cited by examiner

FIG. IA
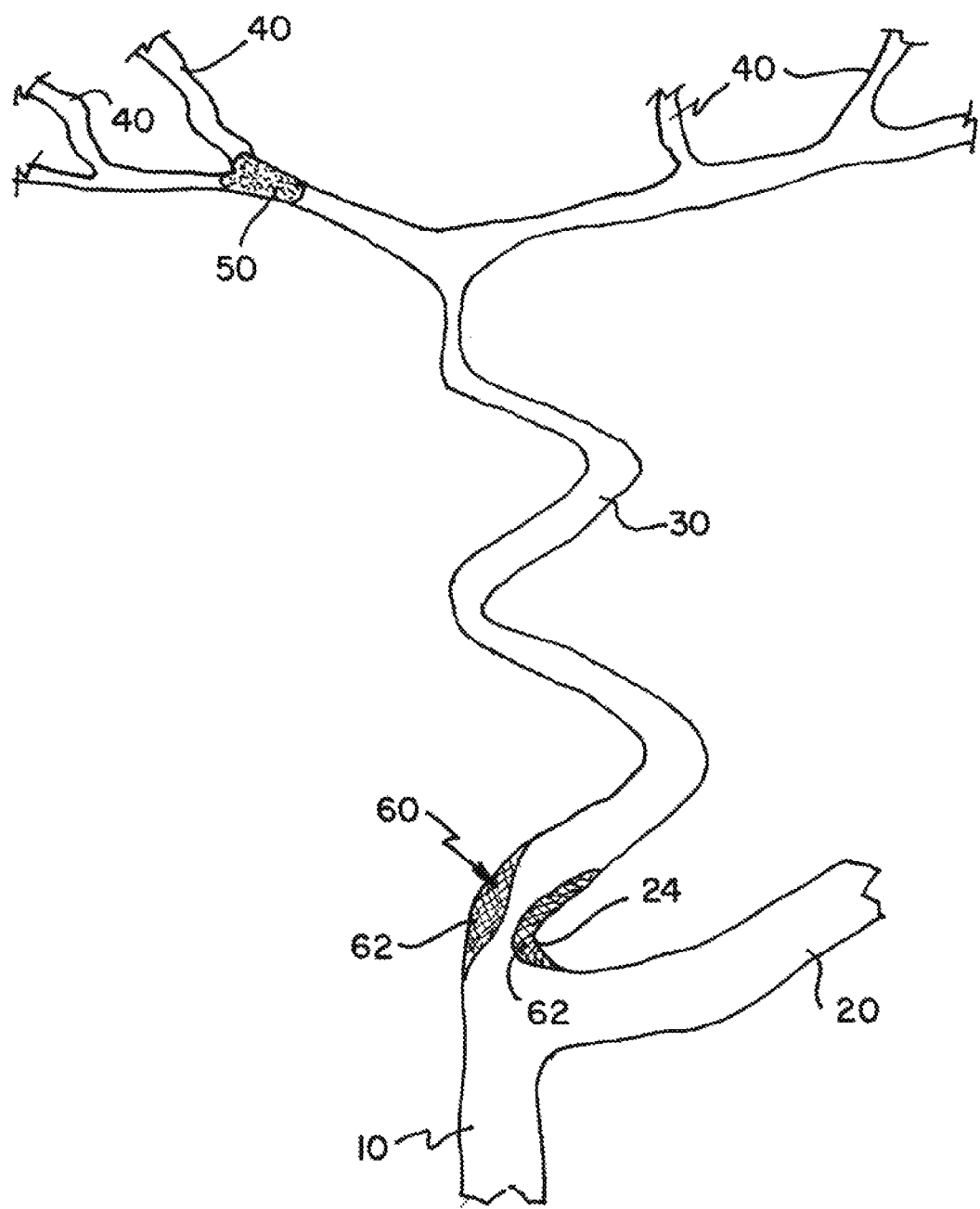

FIG. IB
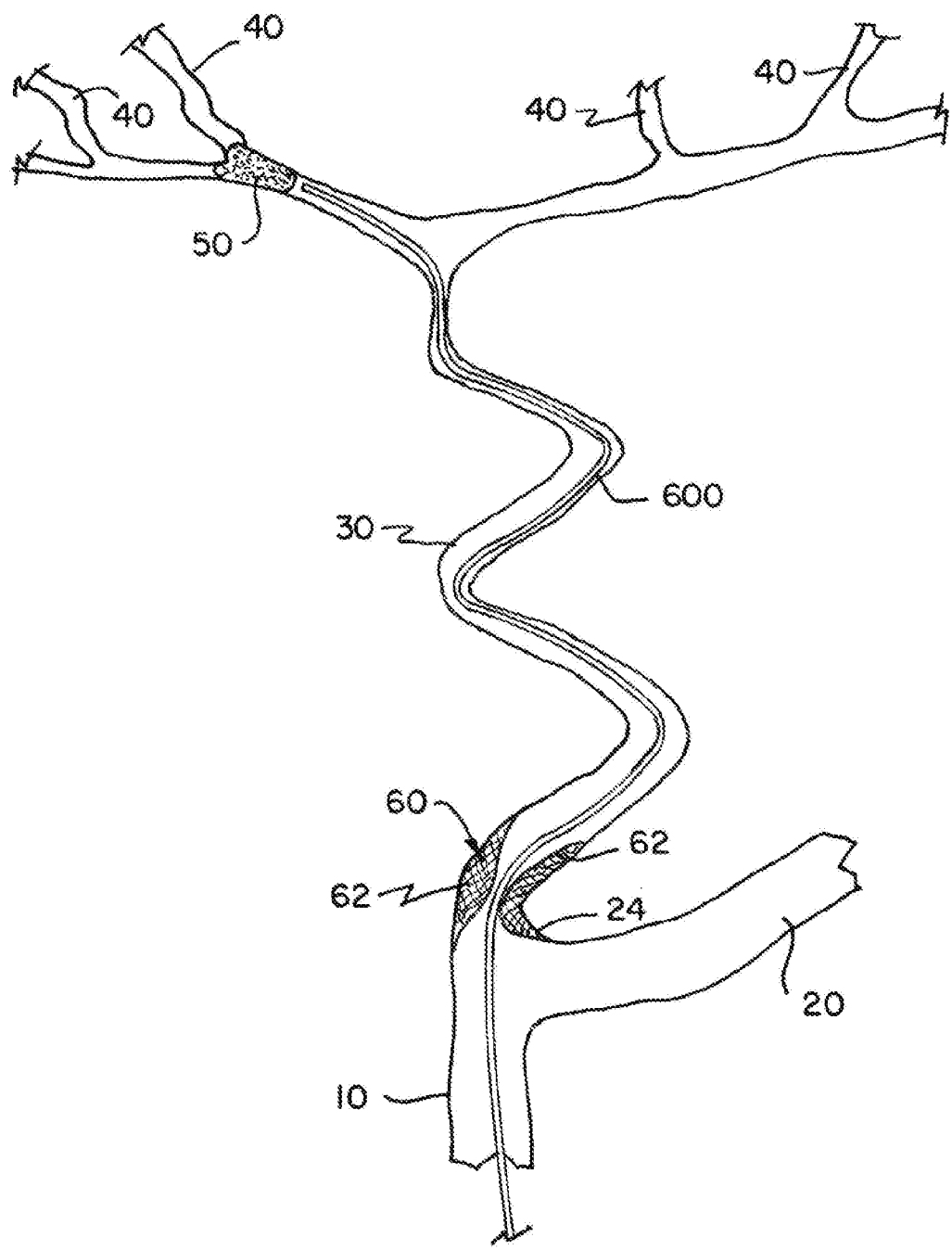

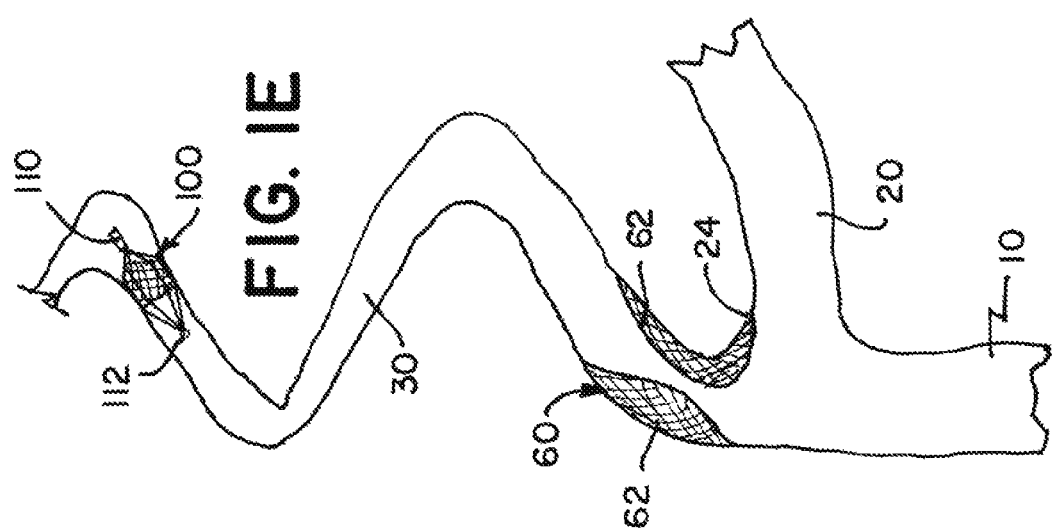
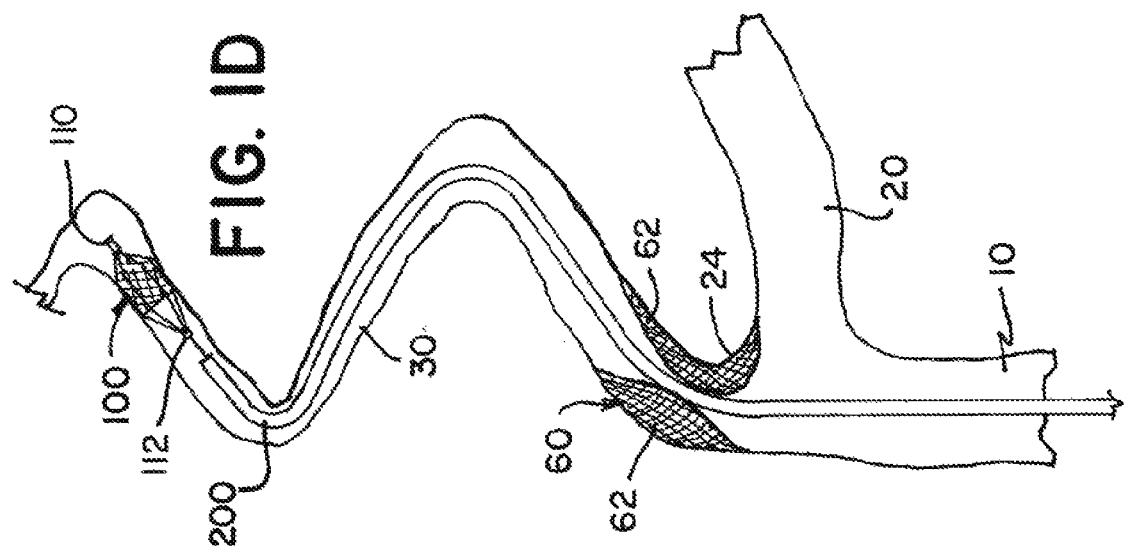
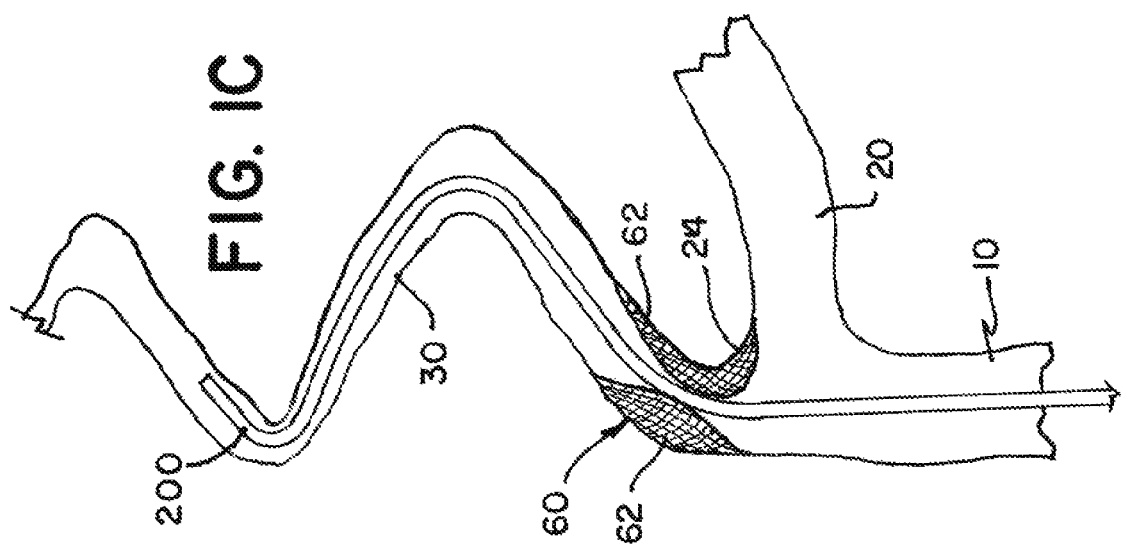

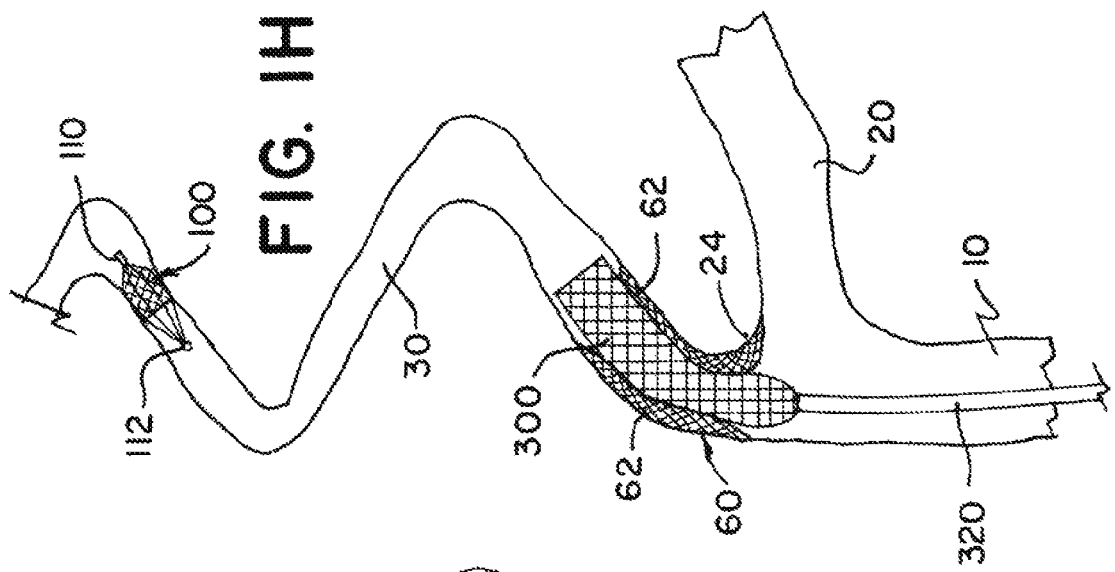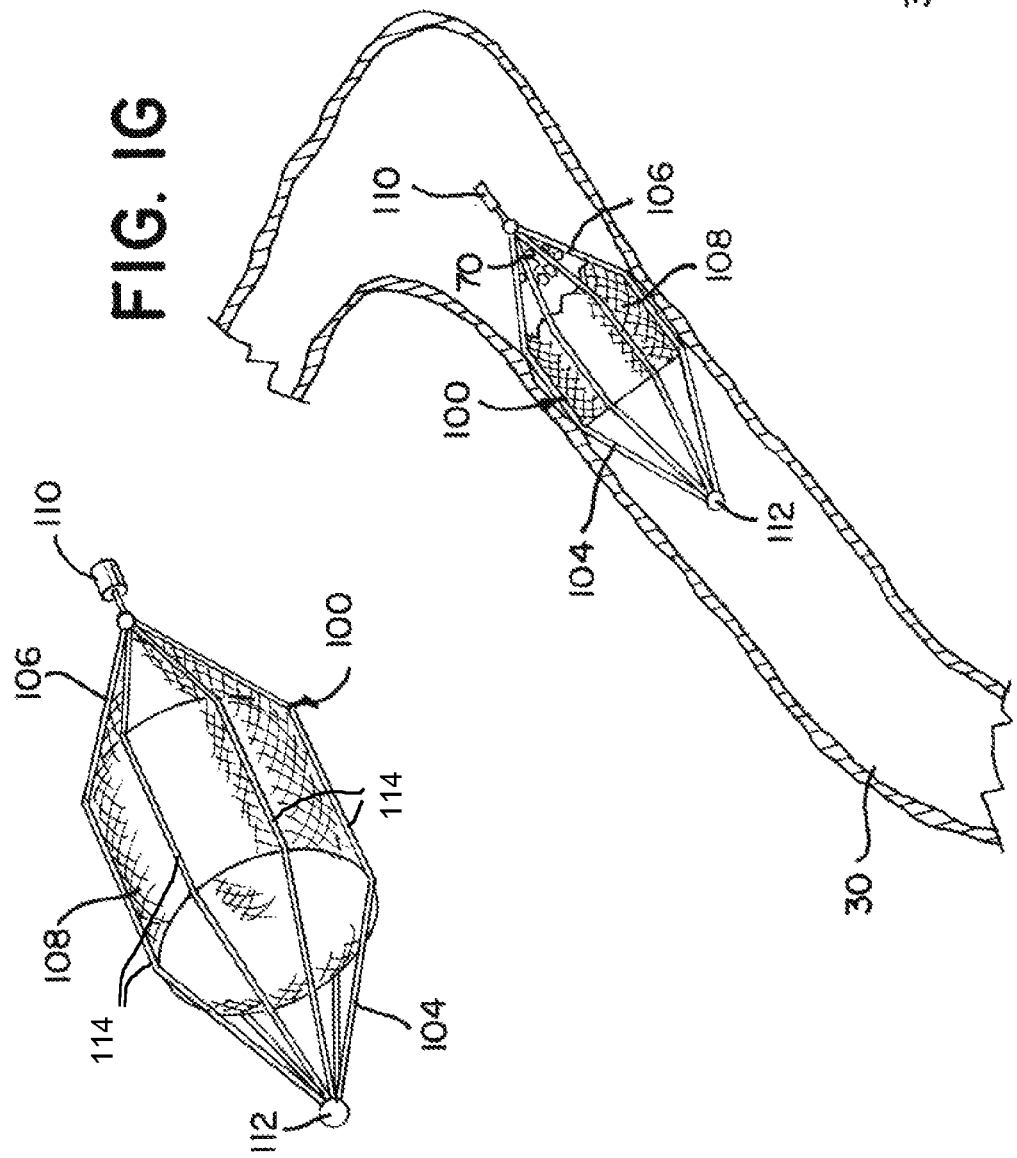

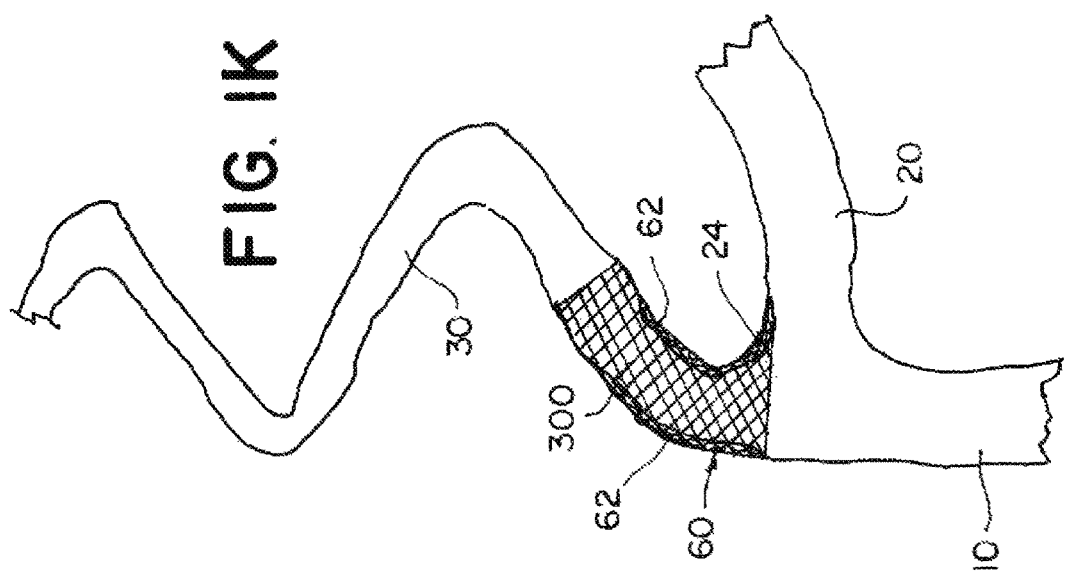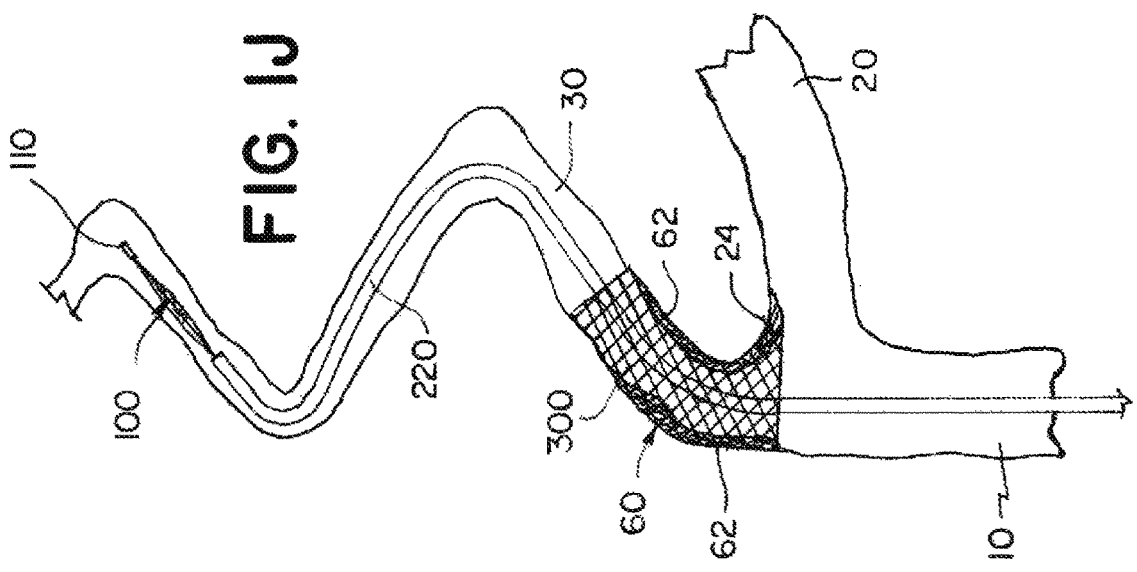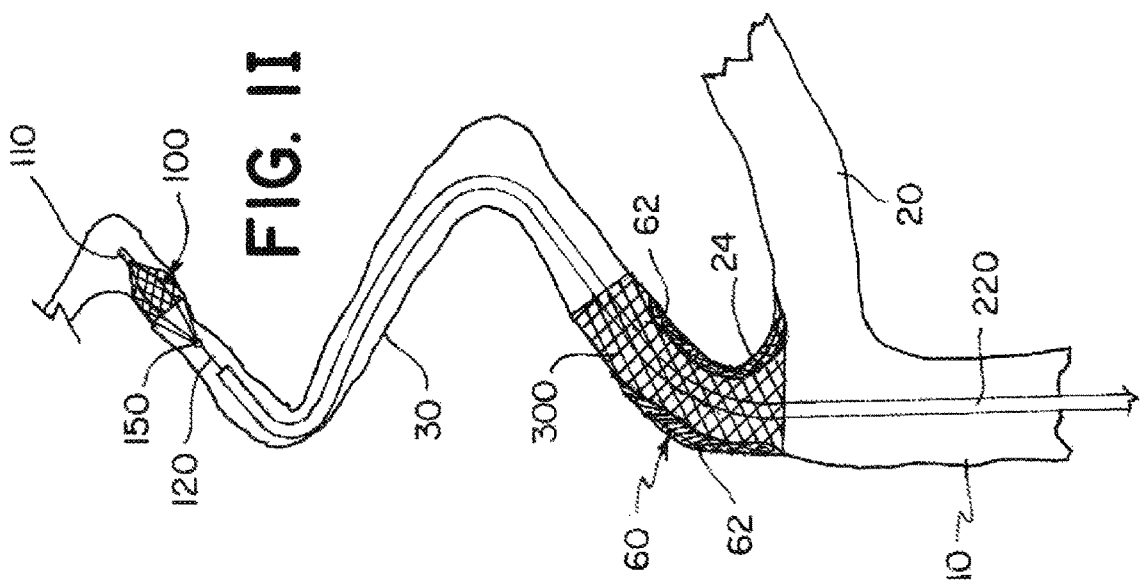

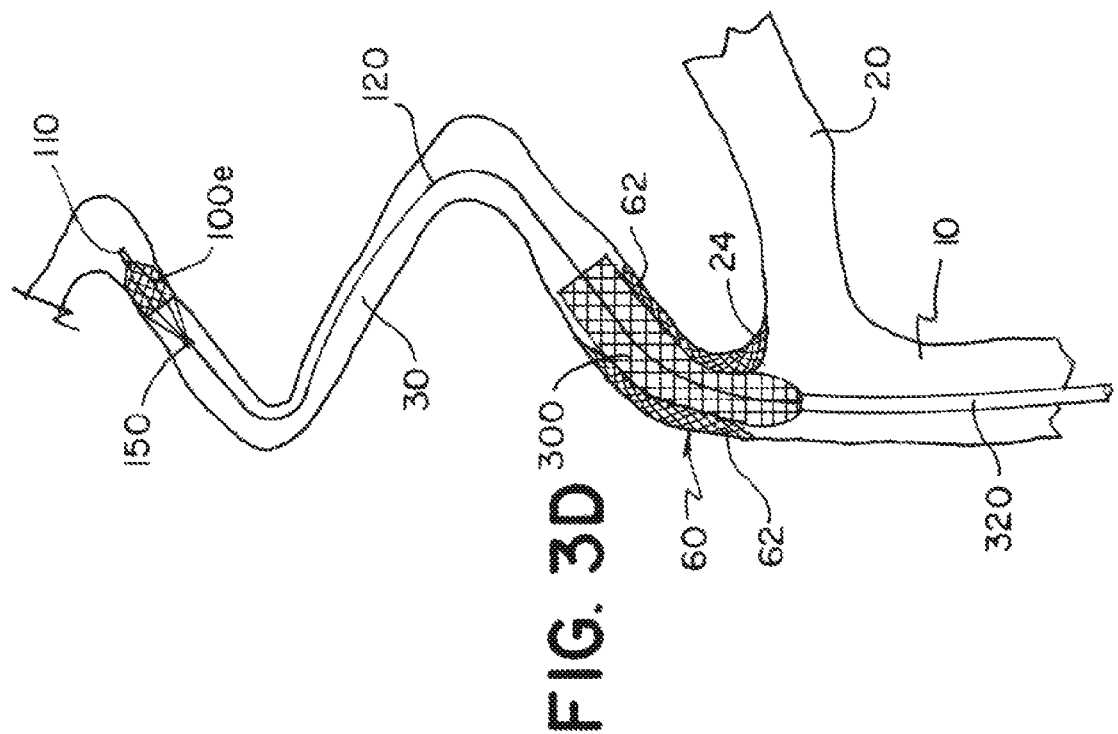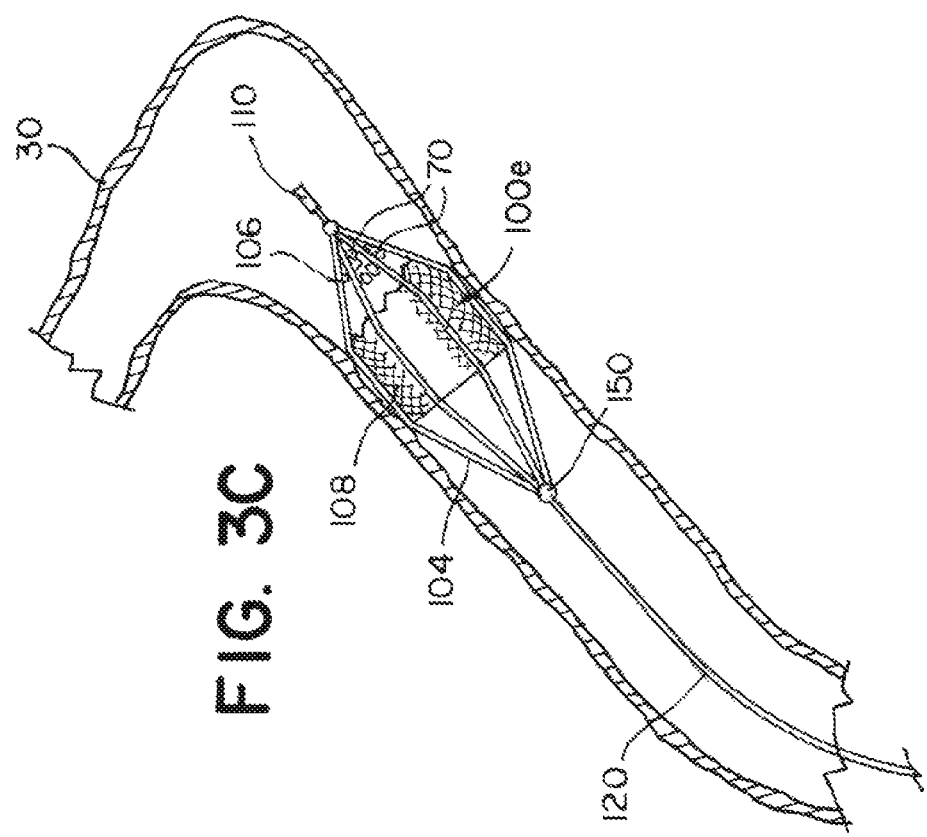

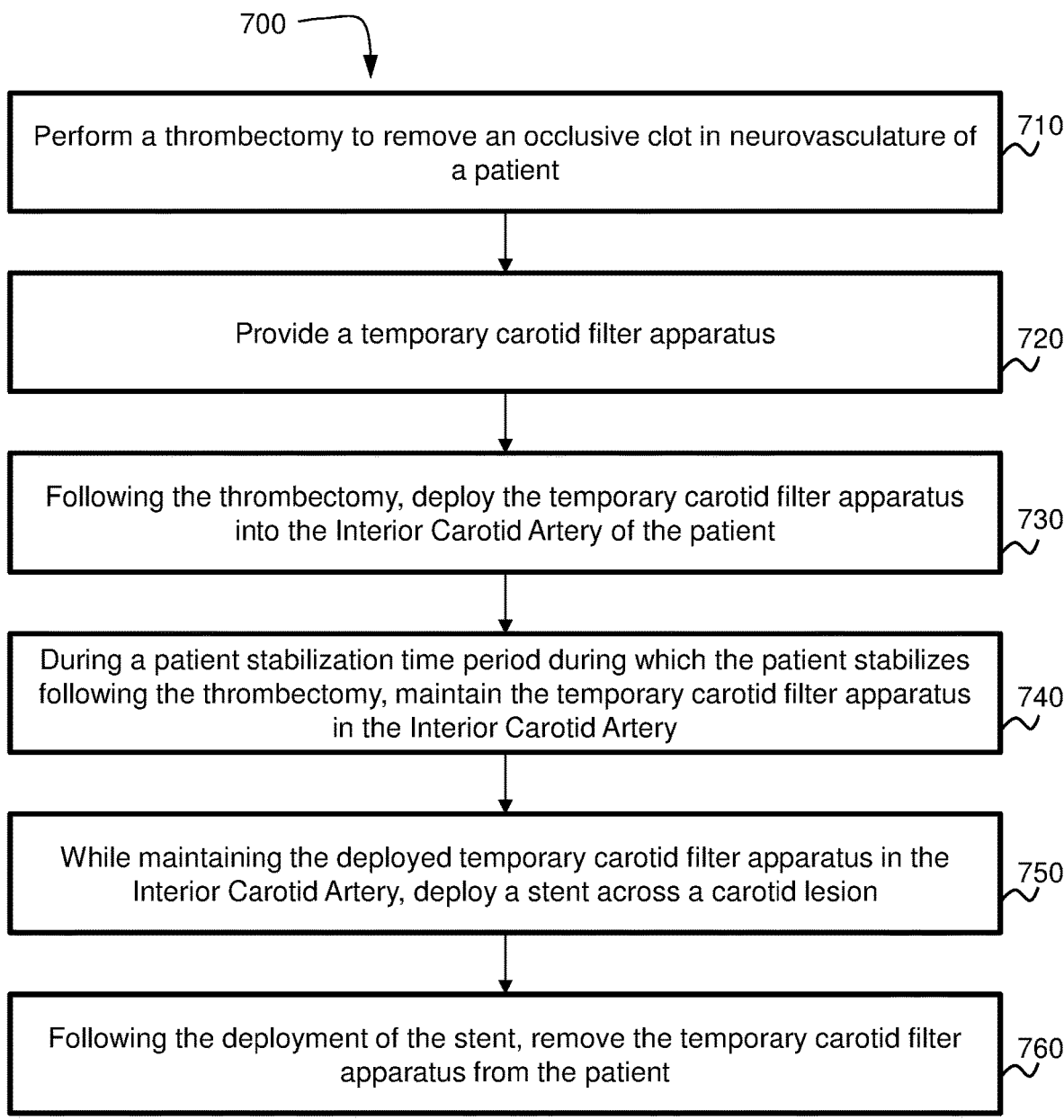

FLOATING CAROTID FILTER

FIELD OF INVENTION

The present invention generally relates to medical devices and procedures for vascular intervention, and more particularly, to devices and treatments for thromboembolic disorders and for removal of foreign bodies in the vascular system.

BACKGROUND

The term "stroke" is used to describe a medical event whereby blood supply to the brain or specific areas of the brain is restricted or blocked to the extent that the supply is inadequate to provide the required flow of oxygenated blood to maintain function. The brain will be impaired either temporarily or permanently, with the patient experiencing a loss of function such as sight, speech or control of limbs. There are two distinct types of stroke, hemorrhagic and embolic. This invention addresses embolic stroke.

Carotid Artery disease occurs when fatty deposits (plaques) clog blood vessels that deliver blood to the brain and head (Carotid Arteries). The nature of the plaque varies considerably, but in many cases, thrombus can form in the artery or pieces of the plaque can break away from a Carotid Artery (for example from a fatty deposit originating from a carotid lesion in the region of the Internal/External Carotid Artery bifurcation), flow distally, and block blood flow to specific areas of the brain, thereby leading to stroke and neurological impairment. Stroke patients can thereafter present tandem occlusions with a blockage present in the Internal Carotid Artery and a blockage in the neurovascular such as the Middle Cerebral Artery (MCA). The priority of the physician treating patients exhibiting tandem occlusions is to restore blood flow in the neurovasculature, which is typically done by performing a thrombectomy to remove the clot. Treatment of the carotid lesion in the same procedure is not desirable as this usually requires implanting a stent which requires the patient to be given antiplatelet therapy to reduce the risk of thrombosis; however antiplatelet therapy can increase the risk of hemorrhaging in patients who have suffered an acute stroke. To reduce risk of hemorrhage, physicians will often perform a thrombectomy procedure and then wait 24 hours for the patient to stabilize before performing a second procedure to stent the carotid lesion. During the interim between the first and second procedures, the patient is at risk of suffering another stroke from additional plaque dislodging or thrombus forming at the carotid lesion and flowing into the neurovascular.

SUMMARY

An object of the present invention is to provide devices and methods for reducing the risk of embolic stroke following a thrombectomy in a patient diagnosed with tandem occlusions. According to examples presented herein, shortly after completing a thrombectomy procedure, a temporary carotid filter can be deployed downstream of an occlusion not treated by the thrombectomy (e.g. a carotid lesion having plaque buildup), and the temporary carotid filter can remain in place during the patient's recovery period following the ischemic stroke and until a procedure to treat the remaining occlusion is completed. The temporary carotid filter can anchor in place while deployed with or without being tethered to a wire extending through the patient's Femoral Artery.

An example method for treating tandem vascular occlusions can include a sub-combination or all the following steps presented in no particular order. The method can also include steps not listed here. A thrombectomy can be performed to remove an occlusive clot in neurovasculature of a patient. A temporary carotid filter apparatus can be provided. The temporary carotid filter apparatus can be deployed into the Interior Carotid Artery of the patient following the thrombectomy. The temporary carotid filter apparatus can include a distal portion having a porosity smaller than a porosity of a proximal portion of the temporary carotid filter. While deploying the temporary carotid filter apparatus, the proximal portion can be positioned proximal the distal portion in the Interior Carotid Artery.

A deployment system can be provided. The provided temporary carotid filter apparatus can include a retrieval feature. The retrieval feature can be detachably attached to the deployment system prior to deployment of the temporary carotid filter apparatus. To deploy the temporary carotid filter apparatus, a portion of the temporary carotid filter apparatus can be expanded to engage the Interior Carotid Artery, and the deployment system can be detached from the retrieval feature.

Additionally, or alternatively to utilizing the deployment system to deploy the temporary carotid filter apparatus, the temporary carotid filter apparatus can include a connection point positioned at a proximal end of the temporary carotid filter apparatus and a pull wire extending proximally from the connection point. A proximal end of the pull wire can be positioned outside the patient or be otherwise positioned to exit the patient.

During a patient stabilization time period, the temporary carotid filter apparatus can be maintained in the Interior Carotid Artery while the patient stabilizes following the ischemic stroke and thrombectomy. A stent can be deployed at a carotid lesion while the deployed temporary carotid filter apparatus is maintained in the Interior Carotid Artery. If the deployed carotid filter apparatus is connected to the pull wire, the stent can be guided through the patient over the pull wire. An embolic mass can be allowed to pass through the proximal portion of the deployed temporary carotid filter apparatus and can be captured by the distal portion of the deployed temporary carotid filter apparatus.

The temporary carotid filter apparatus can be removed from the patient following the deployment of the stent. A retrieval system and a retrieval catheter can be provided for retrieving the temporary carotid filter apparatus. To remove the temporary carotid filter apparatus, the deployment system can be attached to the retrieval feature, the retrieval system and the temporary carotid filter apparatus can be pulled proximally into the retrieval catheter, and the temporary carotid filter apparatus, retrieval system, and retrieval catheter can be withdrawn from the patient.

An example method for treating a patient having a neurovascular occlusion and a carotid lesion include a sub-combination or all the following steps presented in no particular order. The method can also include steps not listed here.

The neurovascular occlusion can be removed from one of the patient's Middle Cerebral Artery, Anterior Cerebral Artery, distal Internal Carotid Artery or posterior neurovasculature.

A temporary carotid filter can be deployed into the Interior Carotid Artery distal the carotid lesion following the removal of the neurovascular occlusion. The temporary carotid filter can be deployed upstream, or proximal to the patient's Circle of Willis.

The temporary carotid filter can have a retrieval feature. A deployment system can be provided. The deployment system can be detachably attached to the retrieval feature. To deploy the temporary carotid filter, the temporary carotid filter can be pushed out of a catheter and into the Interior Carotid Artery, the temporary carotid filter can be expanded to engage the Interior Carotid Artery, and the deployment system can be detached from the retrieval feature of the temporary carotid filter.

Additionally, or alternatively to utilizing a retrieval feature to deploy the temporary carotid filter, the temporary carotid filter can have an expandable filter portion and a pull wire extending proximally from the expandable filter portion. To deploy the temporary carotid filter, the expandable filter portion can be expanded in the Interior Carotid Artery, and a proximal end of the pull wire can be positioned outside the patient or otherwise positioned to exit the patient.

The temporary carotid filter can be maintained in the Interior Carotid Artery at least until the patient stabilizes following the removal of the neurovascular occlusion. The temporary carotid filter can be maintained in the Interior Carotid Artery approximately 24 hours. An embolic mass can be captured within the temporary carotid filter while the deployed temporary carotid filter is maintained in the Interior Carotid Artery. A stent can be deployed across the carotid lesion while the deployed temporary carotid filter is maintained in the Interior Carotid Artery. If the temporary carotid filter has a pull wire, the stent can be guided through the patient over the pull wire while the deployed temporary carotid filter is maintained in the Interior Carotid Artery. After the removal of the neurovascular occlusion and before the patient stabilizes from the removal of the neurovascular occlusion, thrombus liberated from the carotid lesion can be captured with the expandable filter portion.

The temporary carotid filter can be removed from the patient following the deployment of the stent.

If the temporary carotid filter has a retrieval feature, to remove the temporary carotid filter from the patient, a retrieval system can be provided, the retrieval system can be attached to the retrieval feature of the temporary carotid filter, and the retrieval system can be pulled proximally to remove the temporary carotid filter from the patient.

An example method for using a temporary carotid filter can include a sub-combination or all the following steps presented in no particular order. The method can also include steps not listed here. A thrombectomy can be performed on a patient. Following the thrombectomy and before the patient stabilizes to safely receive antiplatelet therapy, the temporary carotid filter can be deployed in a distal Carotid Artery of the patient. After the temporary carotid filter is deployed and at least until the patient stabilizes to safely receive antiplatelet therapy, the temporary carotid filter can be maintained in the distal Carotid Artery. While the temporary carotid filter is in the distal Carotid Artery, a carotid lesion in the patient can be treated. Once the carotid lesion is treated, the temporary carotid filter can be extracted from the patient.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 1A through 1K are illustrations of example steps for treating tandem occlusions with an exemplary floating temporary carotid filter according to aspects of the present invention;

FIGS. 3A through 3G are illustrations of example steps for treating tandem occlusions with an exemplary tethered temporary carotid filter according to aspects of the present invention; and FIG. 4 is a flow diagram listing example method steps for using a temporary carotid filter according to aspects of the present invention.

DETAILED DESCRIPTION

Figure 2A:
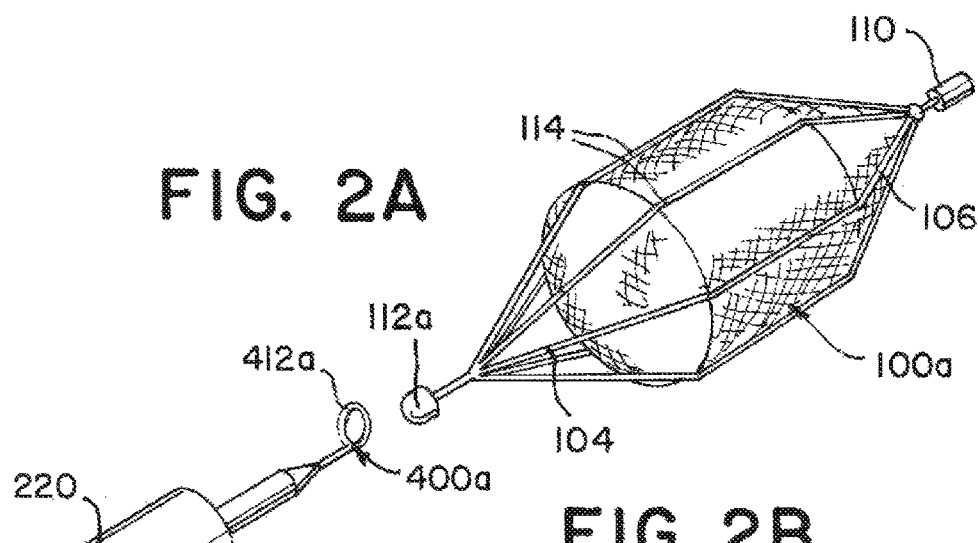
FIGS. 2A through 2D are illustrations of exemplary floating temporary carotid filters having an engagement feature and exemplary retrieval and/or deployment systems according to aspects of the present invention.

Examples described herein generally include a temporary carotid filter which can be deployed in the Interior Carotid Artery to catch any thrombus which may be liberated from a carotid lesion in the period between a thrombectomy procedure and stenting of the carotid lesion. The filter can be introduced and deployed at the end of the thrombectomy procedure, and the filter can catch thrombus in the blood from in the Carotid Artery. When deployed, the carotid filter can be detached and left floating in the vessel, or the carotid filter can be tethered to a proximal shaft. The carotid filter can be left in position in the vascular for a period of time while the patient recovers from the thrombectomy. If the filter gets blocked, this need not cause a significant issue as the flow is already reduced due to significant narrowing of the Interior Carotid Artery and collateral flow is available through the Circle of Willis. If the filter is attached with a wire to a proximal shaft, the wire can be used as a guidewire to introduce a stent delivery system. The stent can be delivered over the guidewire according to methods currently practiced with current carotid filters. After the stenting procedure, the filter can be captured by a retrieval catheter and removed together with thrombus it has captured. The floating version of the filter can include a proximal feature to engage with the retrieval catheter or a retrieval system for ease of removal.

FIGS. 1A through 1K are illustrations of example steps for treating tandem occlusions with an exemplary floating temporary carotid filter 100. FIG. 1A illustrates vasculature of a patient having tandem occlusions including an occlusive clot 50 in a neurovasculature 40 vessel and plaque 62 forming a second occlusion at a carotid lesion 60. The carotid lesion 60 can be positioned at a bifurcation 24 of a Common Carotid Artery 10 to an Internal Carotid Artery 30 and an External Carotid Artery 20. The carotid lesion 60 can be positioned in the Internal Carotid Artery 30 or Common Carotid Artery 10.

FIG. 1B illustrates a catheter 600 inserted in the patient's vasculature and positioned to extract the occlusive clot 50 in the neurovasculature 40. A thrombectomy procedure can be performed using a stent retriever if required, and the clot 50 can be pulled into the catheter 600 for extraction. The catheter 600 can be extracted or repositioned.

FIG. 1C illustrates a catheter 200 positioned to deliver a temporary carotid filter within the Internal Carotid Artery 30. The microcatheter or intermediate catheter 200 can be positioned and the temporary carotid filter can be delivered shortly after the occlusive clot 50 is extracted, or at the end of the thrombectomy procedure. The catheter 200 can be a catheter used during the thrombectomy procedure (such as catheter 600 illustrated in FIG. 1B), and/or the catheter 200 can be introduced through an access catheter used during the thrombectomy procedure.

FIG. 1D illustrates a temporary carotid filter apparatus 100 deployed from the filter delivery catheter 200 into the Internal Carotid Artery 30 downstream of the carotid lesion 60. The carotid filter apparatus 100 can be a floating filter that maintains its position in the Internal Carotid Artery 30 by anchoring to sidewalls of the Internal Carotid Artery 30. The floating filter apparatus 100 can be detachably attached to a delivery system during delivery and detached from the delivery system once it is anchored within the Internal Carotid Artery 30.

FIG. 1E illustrates the floating filter apparatus 100 maintaining its position in the Internal Carotid Artery 30 after extraction of the filter delivery catheter 200. The floating filter apparatus 100 can be left in place, maintaining its position while the patient recovers from the thrombectomy. The floating filter can be left in place at least until the patient is recovered to safely receive a Carotid Stent and antiplatelet therapy.

FIG. 1F illustrates the floating filter apparatus 100 in an expanded condition sized to anchor within vasculature of the patient. The apparatus 100 can include a radiopaque marker 110, a porous distal portion 106 having a porosity 102 (see FIGS. 2B and 2C) small enough to capture liberated thrombus 70 and large enough to allow sufficient blood flow, an expandable portion 108 that can extend to anchor the apparatus 100, a proximal portion 104 with a porosity large enough to allow liberated thrombus to pass through, struts 114 forming a body frame, and a retrieval feature 112 for detachably attaching to a delivery system and/or a retrieval system. Pores in the distal portion 106 and the proximal portion can be spaces between a mesh material, openings in a laser cut apparatus, a spacing between struts, etc.

FIG. 1G illustrates the floating filter apparatus 100 capturing liberated thrombus 70 while maintaining its position in the vasculature. By allowing the thrombus 70 to travel through the proximal portion 104 and be blocked by the distal portion 106, the floating filter 100 can capture the liberated thrombus 70 within its body. The collected thrombus 70 can be contained by the floating filter 100 while the filter 100 maintains its position and when the filter 100 is extracted from the patient.

If the filter accumulates a significant amount of thrombus 70, the filter can become blocked. However, given the patient already suffers an occlusion at the carotid lesion 60, blood flow is already reduced, and blockage of the filter need not present a blockage issue that is more significant than the blockage at the carotid lesion 60. Further, collateral flow is available through the Circle of Willis so a blockage in the Carotid Artery is typically less harmful to the patient than the thrombus migrating to the neurovasculature and causing a second ischemic stroke.

The retrieval feature 112 can be positioned at the proximal portion 104, near the filter's proximal end. The retrieval feature 112 can serve as a connection point for detaching from a delivery system and/or attaching to a retrieval system.

Once the patient has recovered from the thrombectomy and is stabilized to receive treatment of the carotid lesion 60, the carotid lesion can be treated.

FIG. 1H illustrates the carotid lesion 60 treated by stenting. During the treatment, a stent 300 can be delivered by a stent deploy catheter 320 and placed across the carotid lesion 60. During stenting, plaque 62 can become dislodged and flow downstream. The dislodged plaque can be captured by the floating carotid filter 100.

FIG. 1I illustrates a filter retrieval catheter 220 positioned to retrieve the carotid filter apparatus 100 following the stenting of the carotid lesion 60. The retrieval catheter 220 can be a catheter used during stenting of the carotid lesion 60. A retrieval system can be provided and delivered through the retrieval catheter 220 to the floating carotid filter 100. The retrieval system can engage the engagement feature 112 of the floating carotid filter 100 in preparation for extraction of the carotid filter apparatus 100.

FIG. 1J illustrates the temporary carotid filter apparatus 100 being pulled proximally into the retrieval catheter 220. The retrieval system can engage the carotid filter 100, and the filter 100 can be pulled proximally by pulling the retrieval system proximally. Thrombus in the temporary carotid filter apparatus can be pulled into the retrieval catheter 220 as the temporary carotid filter apparatus 100 is pulled proximally into the retrieval catheter 220. The filter 100, captured thrombus, retrieval system, and catheter 220 can be extracted from the patient.

FIG. 1K illustrates the stented carotid lesion 60 following treatment of the tandem occlusions.

Figure 2B:
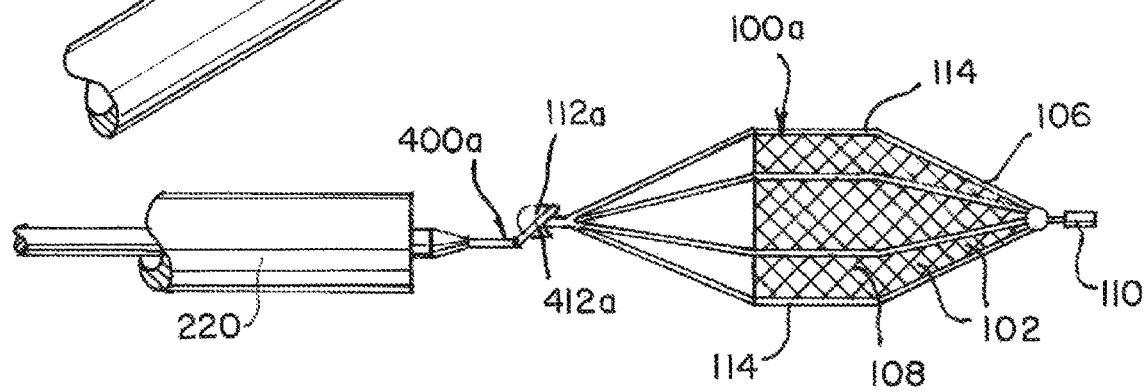

FIGS. 2A through 2D are illustrations of exemplary floating temporary carotid filters 100*a*, 100*b* having an engagement feature 112*a*, 112*b* and exemplary retrieval and/or deployment systems 400*a*, 400*b*. FIGS. 2A and 2B illustrate a floating temporary carotid filter 100*a* having an engagement/retrieval feature 112*a* that can be engaged to a looped wire 412*a*. The engagement feature 112*a* be a bump or a protrusion at a proximal end of the filter 100*a*, and the looped wire 412*a* can encircle the engagement feature 112*a*. To engage the looped wire 412*a* to the engagement feature 112*a*, the looped wire 412*a* can be lassoed around the protrusion. The looped wire 412*a*, once lassoed, can engage a notch. Additionally, or alternatively, the looped wire 412*a*, once lassoed, can be tightened by retracting the wire into a tube so that the engagement feature 112*a* prevents the looped wire 412*a* from sliding proximally off of the engagement feature 112*a*. To release the engagement feature 112*a*, the looped wire 412*a* can disengage the protrusion and the loop 412*a* can be slid proximally off of the engagement feature 112*a*.

Figure 2C:
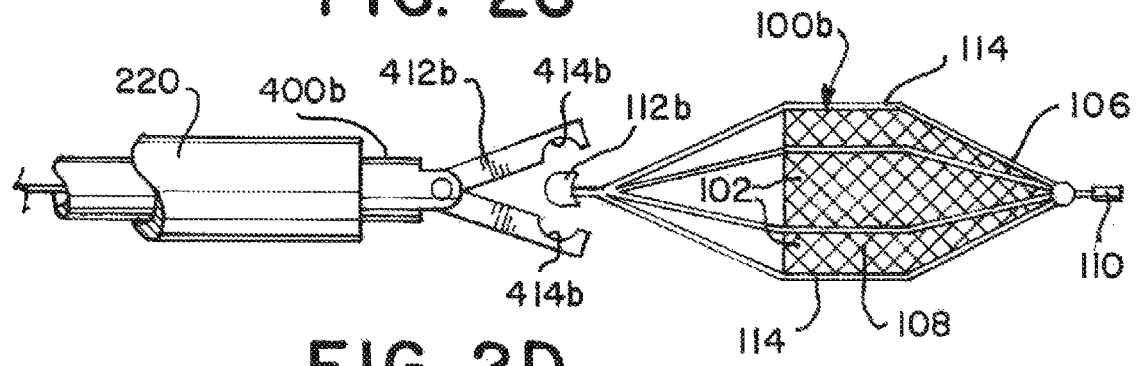
Figure 2D:
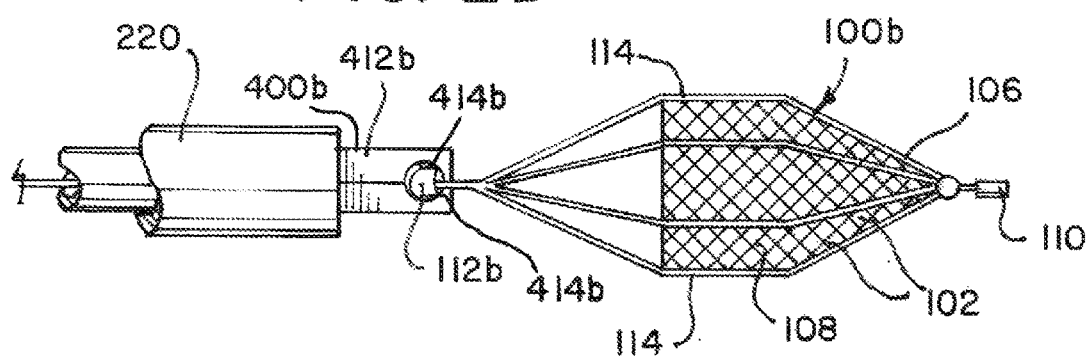

FIGS. 2C and 2D illustrate a floating temporary carotid filter 100*b* having an engagement/retrieval feature 112*b* that can be grabbed by two or more arms 412*b*. During delivery, the engagement feature 112*b* can be held between indentations 414*b* in the arms 412*b*. The arms 412*b* can be forced to stay together due to the dimensions of the catheter 220 as the system 400*b* is delivered through the retrieval catheter 220. As the arms 412*b* exit a distal end of the catheter 220, the arms 412*b* can spread apart, releasing the engagement feature 112*b*. During retrieval, the arms 412*b* can be positioned out of the catheter 220 and spread apart around the engagement feature 112*b*. The catheter 220 can be pushed distally, or the arms 412*b* can be pulled proximally to cause the arms 412*b* to approach each other and grab the engagement feature 112*b* with the indentations 414*b*. Then, the retrieval system 400*b* and filter 100*b* can be pulled proximally into the catheter 220, or, if the catheter 220 is too small to accommodate the filter 100*b*, the catheter 220, retrieval system 400*b*, and filter 100*b* can be pulled proximally into a larger catheter.

Figure 3B:
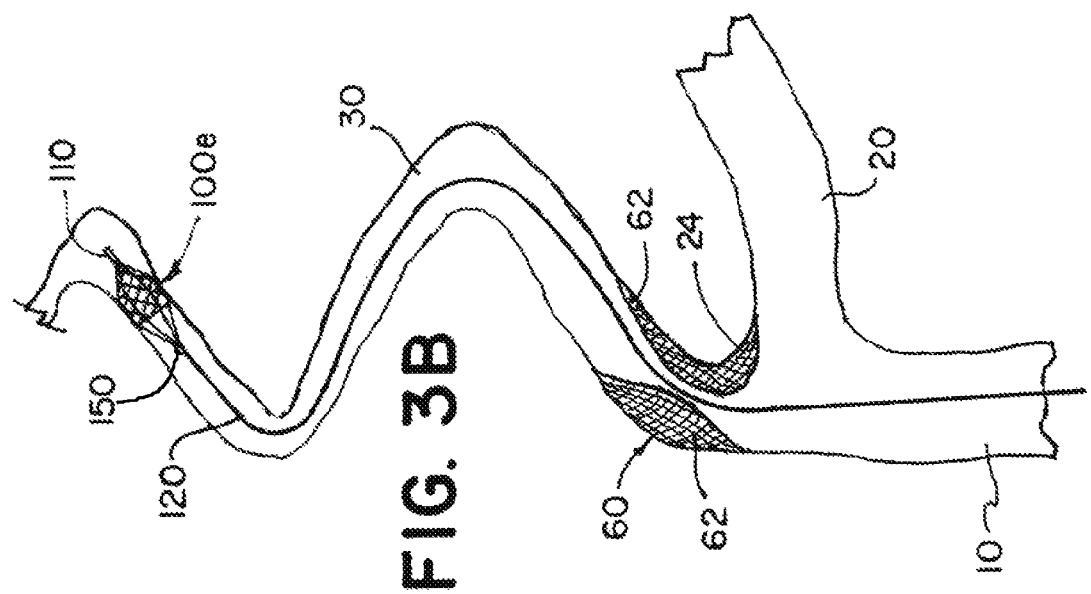
Figure 3A:
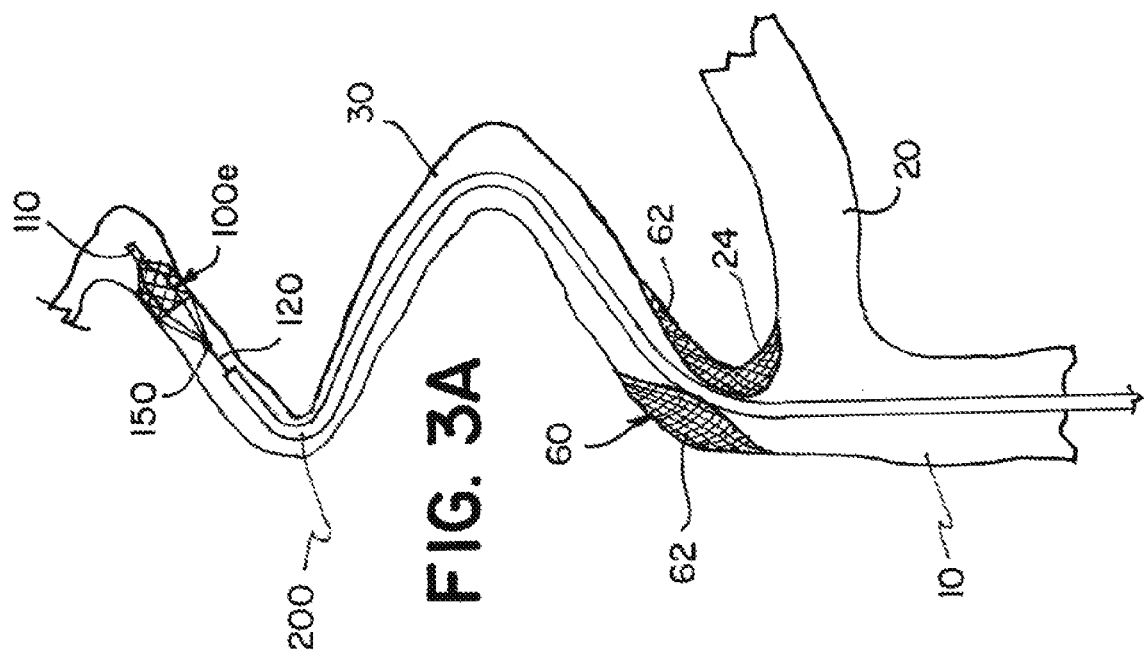

FIGS. 3A through 3G are illustrations of example steps for treating tandem occlusions with an exemplary tethered temporary carotid filter 100e. A patient having tandem occlusions such as illustrated in FIG. 1A can be treated to remove the clot 50 in the neurovasculature 40, and, as illustrated in FIG. 3A, while the patient is recovering from the thrombectomy, the temporary carotid filter 100e can be implanted in the Internal Carotid Artery 30 through a catheter 200.

FIG. 3B illustrates the tethered filter apparatus 100e maintaining its position in the Internal Carotid Artery 30 downstream of the carotid lesion 60 after extraction of the filter delivery catheter 200. The tethered filter apparatus 100e can be left in place, maintaining its position while the patient recovers from the thrombectomy. The tethered filter 100e can be left in place at least until the patient is recovered to safely receive a Carotid Stent and antiplatelet therapy. A wire 120 can serve to maintain the position of the filter 100e in the Internal Carotid Artery 30 and/or provide a means for extracting the filter 100e from the Internal Carotid Artery 30. The temporary carotid filter 100e can additionally or alternatively anchor to the sidewalls of the Internal Carotid Artery 30 to maintain its position. The wire 120 can be tethered to a proximal shaft.

FIG. 3C illustrates the tethered filter apparatus 100e capturing liberated thrombus 70 while maintaining its position in the vasculature. The tethered filter apparatus 100e can have pores. The pores can be spaces between a mesh material, openings in a laser cut apparatus, spaces between struts 114, etc. The tethered filter apparatus 100e can have a distal portion 106 with pores 102 (see FIGS. 2B and 2C) sized small enough to capture the liberated thrombus 70, and the tethered filter apparatus 100e can have a proximal portion 104 with pores sized large enough to allow the liberated thrombus 70 to pass therethrough. By allowing the thrombus 70 to travel through the proximal portion 104 and be blocked by the distal portion 106, the filter 100e can capture the liberated thrombus 70 within its body. The collected thrombus 70 can be contained by the filter 100e while the filter 100e maintains its position and when the filter 100e is extracted from the patient.

The tethered filter apparatus 100e can have a connection point 150 positioned at the proximal portion 104, near the filter's proximal end. The connection point 150 can be attached to the wire 120.

Once the patient has recovered from the thrombectomy and is stabilized to receive treatment of the carotid lesion 60, the carotid lesion can be treated.

FIG. 3D illustrates the carotid lesion 60 being treated by stenting. During the treatment, a stent 300 can be delivered by a stent deploy catheter 320 and placed across the carotid lesion 60. The wire 120 can serve as a guidewire for delivery of the stent 300 to the site of the carotid lesion 60. During stenting, plaque 62 can become dislodged and flow downstream. The dislodged plaque can be captured by the temporary carotid filter 100e.

Figure 3G:
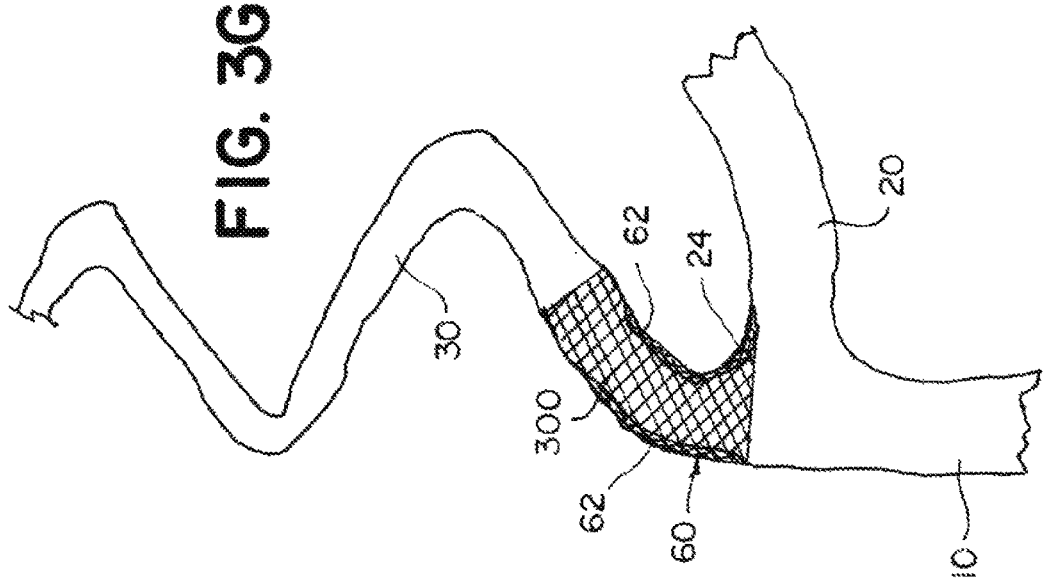
Figure 3F:
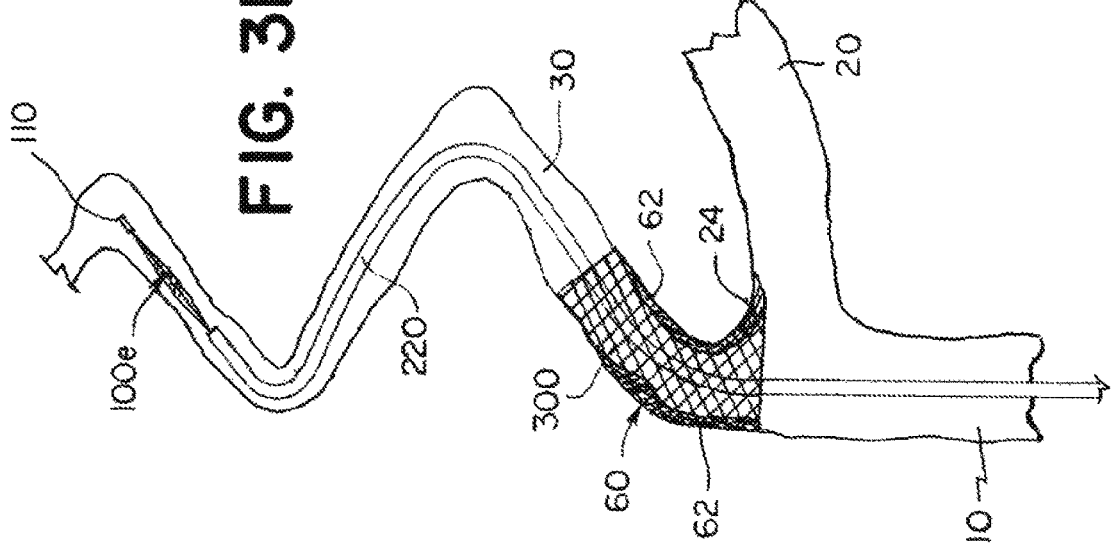
Figure 3E:
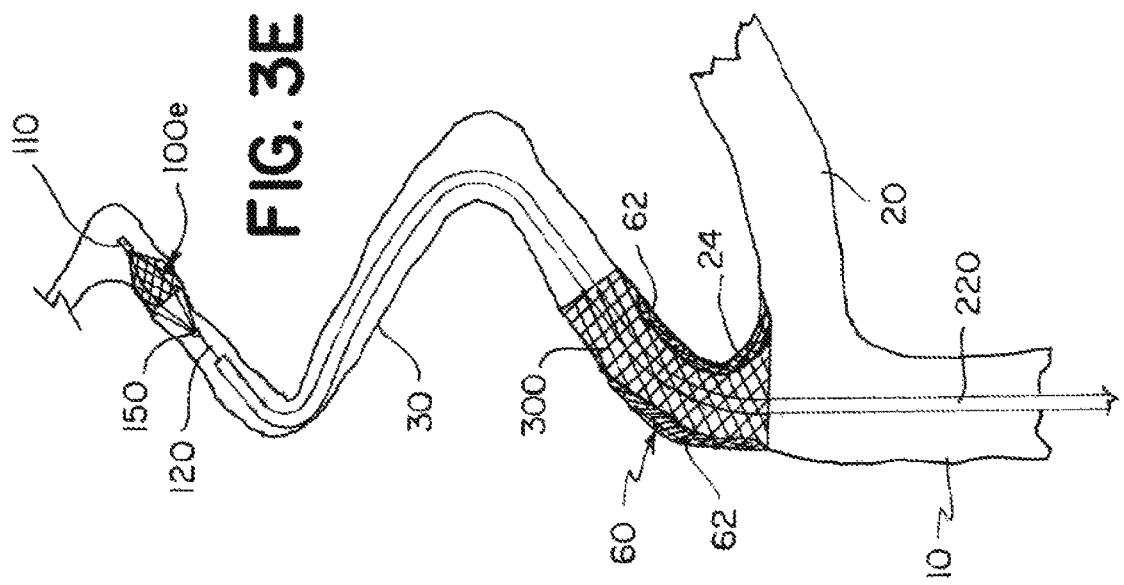

FIG. 3E illustrates a filter retrieval catheter 220 positioned to retrieve the carotid filter apparatus 100e following the stenting of the carotid lesion 60. The retrieval catheter 220 can be a catheter used during stenting of the carotid lesion 60.

FIG. 3F illustrates the temporary carotid filter apparatus 100e being pulled proximally into the retrieval catheter 220. The temporary carotid filter 100e can be pulled proximally by pulling the pull wire 120 proximally. Thrombus in the temporary carotid filter apparatus 100e can be pulled into the retrieval catheter 220 as the temporary carotid filter apparatus 100e is pulled proximally into the retrieval catheter 220. The filter 100e, captured thrombus, and catheter 220 can be extracted from the patient.

FIG. 3G illustrates the stented carotid lesion 60 following treatment of the tandem occlusions.

FIG. 4 is a flow diagram outlining example method steps for using a temporary carotid filter. The method steps can be implemented by combinations of example devices presented herein or by other means as would be known to one of ordinary skill in the art.

Referring to method 700 outlined in FIG. 4, in step 710, a thrombectomy can be performed to remove an occlusive clot in neurovasculature of a patient. In step 720, a temporary carotid filter apparatus can be provided. In step 730, following the thrombectomy, the temporary carotid filter apparatus can be deployed into the Interior Carotid Artery of the patient. In step 740, during a patient stabilization time period during which the patient stabilizes following the thrombectomy, the temporary carotid filter apparatus can be maintained in the Interior Carotid Artery. In step 750, while maintaining the deployed temporary carotid filter apparatus in the Interior Carotid Artery, a stent can be deployed across a carotid lesion. In step 760, following the deployment of the stent, the temporary carotid filter apparatus can be removed from the patient.

The descriptions contained herein are examples of embodiments of the invention and are not intended in any way to limit the scope of the invention. As described herein, the invention contemplates variations and modifications of a temporary carotid filter and methods for using the same, including alternative carotid filter frames, structures, filter pore material and construction, alternative means for deploying, maintaining, and extracting the carotid filter, etc. These modifications would be apparent to those having ordinary skill in the art to which this invention relates and are intended to be within the scope of the claims which follow.

The invention claimed is:

1. A method for treating tandem vascular occlusions, the method comprising:
    performing a thrombectomy to remove an occlusive dot in neurovasculature of a patient; providing a temporary carotid filter apparatus;
    deploying the temporary carotid filter apparatus into the interior Carotid Artery of the patient following the thrombectomy;
    maintaining the temporary carotid filter apparatus in the interior Carotid Artery during a patient stabilization time period during which the patient stabilizes following the thrombectomy;
    deploying a stent approximate a carotid lesion after maintaining the deployed temporary carotid filter apparatus in the Interior Carotid Artery for approximately 24 hours; and
    removing the temporary carotid filter apparatus from the patient following the deployment of the stent.

2. The method of claim 1, wherein the provided temporary carotid filter apparatus comprises a retrieval feature, the method further comprising:
    providing a deployment system; and
    detachably attaching the deployment system to the retrieval feature of the temporary carotid filter apparatus.

3. The method of claim 2, wherein deploying the temporary carotid filter apparatus comprises:
    expanding a portion of the temporary carotid filter apparatus to engage the Interior Carotid Artery; and detaching the deployment system from the retrieval feature of the temporary carotid filter apparatus.

4. The method of claim 3, further comprising:
allowing an embolic mass to pass through a proximal portion of the deployed temporary carotid filter apparatus; and
capturing the embolic mass with a distal portion of the deployed temporary carotid filter apparatus.

5. The method of claim 3, further comprising:
providing a retrieval system and a retrieval catheter for retrieving the temporary carotid filter apparatus.

6. The method of claim 5, wherein removing the temporary carotid filter apparatus from the patient following the deployment of the stent comprises:
attaching the retrieval system to the retrieval feature of the temporary carotid filter apparatus; and
pulling the retrieval system and the temporary carotid filter apparatus proximally into the retrieval catheter; and
removing the temporary carotid filter apparatus, retrieval system, and retrieval catheter from the patient.

7. The method of claim 1, wherein the provided temporary carotid filter apparatus comprises a proximal portion comprising a first porosity, a distal portion comprising a second porosity smaller than the first porosity, a connection point disposed approximate the proximal portion, and a pull wire extending proximally from the connection point, and
wherein deploying the temporary carotid filter apparatus comprises:
positioning the proximal portion proximal the distal portion in the Interior Carotid Artery; and
positioning the pull wire to exit the patient at a proximal end of the pull wire.

8. The method of claim 7, further comprising:
guiding the stent through the patient over the pull wire.

9. A method for treating a patient having a neurovascular occlusion and a carotid lesion, the method comprising:
removing the neurovascular occlusion;
deploying a temporary carotid filter into the interior Carotid Artery distal the carotid lesion following the removal of the neurovascular occlusion;
maintaining the temporary carotid filter in the interior Carotid Artery at least until the patient stabilizes following the removal of the neurovascular occlusion;
deploying a stent across the carotid lesion after maintaining the deployed temporary carotid filter in the interior Carotid Artery for approximately 24 hours; and
removing the temporary carotid filter from the patient, following the deployment of the stent.

10. The method of claim 9, wherein the provided temporary carotid filter comprises a retrieval feature, the method further comprising:

providing a deployment system; and
detachably attaching the deployment system to the retrieval feature.

11. The method of claim 10, wherein deploying the temporary carotid filter comprises:
unsheathing the temporary carotid filter out of a catheter and into the Interior Carotid Artery;
allowing the temporary carotid filter to expand and engage the Interior Carotid Artery; and
detaching the deployment system from the retrieval feature of the temporary carotid filter.

12. The method of claim 9, further comprising:
capturing an embolic mass within the temporary carotid filter while maintaining the deployed temporary carotid filter in the Interior Carotid Artery.

13. The method of claim 11, wherein removing the temporary carotid filter from the patient comprises:
providing a retrieval system;
attaching the retrieval system to the retrieval feature of the temporary carotid filter; and
pulling the retrieval system proximally to remove the temporary carotid filter from the patient.

14. The method of claim 9, wherein the provided temporary carotid filter comprises an expandable filter portion and a pull wire extending proximally from the expandable filter portion, and
wherein deploying the temporary carotid filter comprises:
expanding the expandable filter portion in the Interior Carotid Artery; and
positioning the pull wire to exit the patient at a proximal end of the pull wire.

15. The method of claim 14, further comprising:
guiding the stent through the patient over the pull wire while maintaining the deployed temporary carotid filter in the Interior Carotid Artery.

16. The method of claim 14, further comprising:
capturing thrombus liberated from the carotid lesion with the expandable filter portion after the removal of the neurovascular occlusion and before the patient stabilizes from ischemic stroke.

17. The method of claim 9, wherein deploying the temporary carotid filter into the Interior Carotid Artery distal the carotid lesion comprises:
deploying the carotid filter into the Interior Carotid Artery proximal to the patient's Circle of Willis.

18. The method of claim 9, wherein removing the neurovascular occlusion comprises:
removing the neurovascular occlusion from one of the patient's Middle Cerebral Artery and the patient's Anterior Cerebral Artery and Internal Carotid Artery.

* * * * *